United States Patent
Steele, Sr. et al.

[11] Patent Number: 5,895,424
[45] Date of Patent: Apr. 20, 1999

[54] PROSTHESIS HAVING AN ALIGNMENT INDICATOR AND METHOD OF USING SAME

[75] Inventors: Martin T. Steele, Sr., Elk River; Timothy B. Petrick, Brooklyn Park, both of Minn.; Michael J. Daugherty, Atlanta, Ga.

[73] Assignee: Mentor Corporation, Santa Barbara, Calif.

[21] Appl. No.: 08/747,223

[22] Filed: Nov. 12, 1996

[51] Int. Cl.⁶ ........................................ A61F 2/04
[52] U.S. Cl. ......................... 623/11; 623/12; 600/40
[58] Field of Search ............................ 623/1, 7, 8, 11, 623/12, 66; 600/40; 128/898; 604/43, 264, 280, 281; 606/185

[56] References Cited

U.S. PATENT DOCUMENTS

| | | | |
|---|---|---|---|
| 2,212,334 | 8/1940 | Wallerich | 18/58 |
| 2,857,915 | 10/1958 | Sheridan | 128/349 |
| 3,086,525 | 4/1963 | Whitcomb | 128/232 |
| 3,190,299 | 6/1965 | Alley et al. | 128/348 |
| 3,295,527 | 1/1967 | Alley et al. | 128/348 |
| 3,369,542 | 2/1968 | Thaidigsman | 128/2 |
| 3,459,189 | 8/1969 | Alley et al. | 128/347 |
| 3,568,817 | 3/1971 | Douglas et al. | 198/33 |
| 3,788,328 | 1/1974 | Alley et al. | 128/350 |
| 3,805,301 | 4/1974 | Liebig | 623/12 |
| 3,875,928 | 4/1975 | Angelchik | 623/66 |
| 3,903,895 | 9/1975 | Alley et al. | 128/350 |
| 4,027,659 | 6/1977 | Slingluff | 128/2 M |
| 4,244,370 | 1/1981 | Furlow et al. | 606/185 |
| 4,279,252 | 7/1981 | Martin | 128/349 |
| 4,545,082 | 10/1985 | Hood | 623/12 |
| 4,704,111 | 11/1987 | Moss | 604/270 |
| 4,795,463 | 1/1989 | Gerow | 623/8 |
| 4,863,470 | 9/1989 | Carter | 623/8 |
| 5,045,071 | 9/1991 | McCormick et al. | 604/280 |
| 5,047,050 | 9/1991 | Arpesani | 623/12 |
| 5,062,417 | 11/1991 | Cowan | 128/79 |
| 5,067,485 | 11/1991 | Cowen | 623/12 |
| 5,167,611 | 12/1992 | Cowan | 600/40 |
| 5,250,020 | 10/1993 | Bley | 600/40 |
| 5,300,120 | 4/1994 | Knapp et al. | 623/11 |
| 5,360,414 | 11/1994 | Yarger | 604/264 |
| 5,405,320 | 4/1995 | Twardwoski et al. | 604/43 |
| 5,423,764 | 6/1995 | Fry | 604/187 |
| 5,632,777 | 5/1997 | Petrick | 623/12 |
| 5,695,517 | 12/1997 | Marin et al. | 623/1 |
| 5,697,970 | 12/1997 | Schmitt et al. | 623/12 |
| 5,704,895 | 1/1998 | Scott et al. | 623/11 |
| 5,718,724 | 2/1998 | Goicoechea et al. | 623/1 |

*Primary Examiner*—Michael J. Milano
*Attorney, Agent, or Firm*—Fish & Richardson P.C., P.A.

[57] ABSTRACT

A method and apparatus comprising placing a visual indicator such as a stripe or series of markings on the tubing connecting the various components of a penile prosthesis to evidence the proper linear alignment of the tubing, and counter-rotating those components prior to or during implantation to achieve or maintain proper alignment of the components and thus prevent or remove any torque on the tubing that would cause tears or separations at the junction points. A tactile indicator may be used in addition to or in place of the visual indicator.

26 Claims, 4 Drawing Sheets

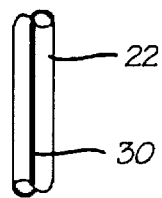
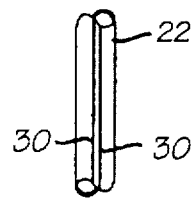
Figure 5      Figure 6
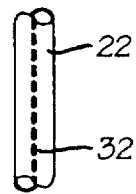
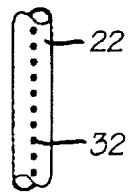
Figure 7      Figure 8
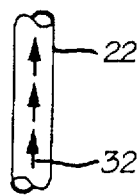
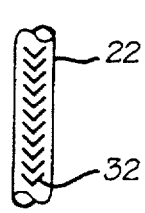
Figure 9      Figure 10
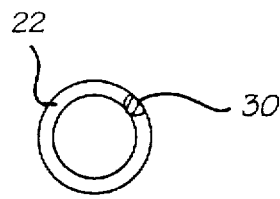
Figure 11
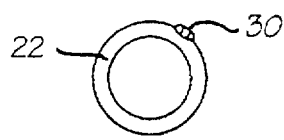
Figure 12

PROSTHESIS HAVING AN ALIGNMENT INDICATOR AND METHOD OF USING SAME

FIELD OF THE INVENTION

The present invention relates generally to the field of implantable penile prosthetic devices, and particularly to an implantable device having a pair of inflatable cylinders for implantation within the corpora cavernosa of a patient, a pump for inflating those cylinders with a fluid, and a reservoir for that fluid.

BACKGROUND OF THE INVENTION

The art relating to penile prosthetic devices is well established, with representative examples of the basic structures of and improvements to such devices being shown in U.S. Pat. No. 5,167,611 to Cowan, U.S. Pat. No. 5,250,020 to Bley, and U.S. Pat. No. 5,062,417 to Cowen. Each of those patents is owned by the assignee of the present application, and suggest various embodiments of a penile prosthesis which have proven operational and commercially suitable.

These examples certainly do not exhaust the structural configurations and functional variations that may be adopted for such a prosthesis, and it is recognized that a wide array of similar products have been developed and are well known to those skilled in the art—emanating both from the assignee of this application and many other individuals and companies.

For purposes of describing the improvement of this invention, it is sufficient to focus on the basic structural components of these representative devices. The common elements include a pair of elongated cylindrical chambers that are implanted within the corpora cavernosa of a patient, and which may be inflated using a biologically compatible fluid to achieve an erection in the patient. The device further includes a reservoir for that fluid, and a pump for transferring fluid from the reservoir to the chambers under pressure. To facilitate operation of the prosthesis, an array of valves must be utilized in combination with the pump to control the flow of the fluid. When the reservoir is located at a remote position relative to the chambers, the reservoir and chambers must be operationally interconnected using tubing or a similar conduit for the fluid. In such devices, it has proven advantageous to locate the pump within the scrotum of the patient, and the reservoir may optionally be located at a remote position such as behind the pelvic wall or combined unitarily with the pump in a Resipump™ design.

One problem associated with such prostheses is the tendency for the tubing forming the fluid conduits to leak or completely separate from the valve block, reservoir, or cylinders. Because the pump and valve block are disposed within the scrotum of the patient where they are subject to more unrestricted freedom of movement as well as intentional manipulation by the patient during operation, the connections between the tubing and valve block appear subject to the greatest potential for damage or separation.

The tubing may remain intact for relatively long periods of time (up to the useful life of the prosthesis), may gradually form a relatively small leak due to a fracture or tear at or near the junction of with another component such as the valve block, or may separate completely from a component without advance warning. The compromise of the closed system may occur in the tubing, at the junction between the tubing and a component, or within the tubing-to-component junction itself. These conditions are probably in an adhered, seated, or molded junction. While forming the tubing or conduits unitarily with the other components will reduce the frequency of leaks and separations compared to devices utilizing bonded connections, it can also unduly increase the overall complexity and cost of manufacturing the prosthesis to unacceptable levels.

SUMMARY OF THE INVENTION

The present invention arises from the unexpected discovery that this tearing and separation are caused not by inherent structural weaknesses or manufacturing defects in the prosthesis itself, but rather by the torque applied to the tubing when the reservoir, pump, or cylinders are twisted or rotated relative to one another prior to or during implantation. After implantation, these torsional forces continue to be exerted—particularly on the connections between the tubing and valve block—and gradually result in the degradation of these connections. The amount of force will generally be proportional to the degree of twisting or rotation of the tubing, and will be compounded by the degree of natural movement of the components and the frequency and manner in which the pump is operated.

Due to the need for relatively thin, flexible tubing forming the fluid conduits—and the relatively large mass of the components such as the reservoir, chambers, and pump compared to that tubing—these torsional forces are not readily apparent to the physician performing the implantation either by visual inspection of the prosthesis or by tactile sensation when holding the components due to the torque being transmitted from the tubing to the components.

Briefly described, the method and apparatus of this invention comprise placing an alignment aid such as a visible stripe or linear series of markings on the tubing connecting the various components of the penile prosthesis, and counter-rotating those components prior to or during the implantation procedure to achieve or maintain proper alignment of those markings and thereby prevent or remove any torsional forces resulting from the inadvertent rotation or twisting of the components relative to one another. A tactile indicator may be used in place of or in addition to the visual indicator.

BRIEF DESCRIPTION OF THE DRAWINGS

FIG. 5 is a broken-away side view of a section of the tubing showing the visual indictor as a continuous line;

FIG. 6 is a broken-away side view of a section of the tubing showing the visual indictor as a pair of parallel continuous lines;

FIG. 7 is a broken-away side view of a section of the tubing showing the visual indictor as series of dashes;

FIG. 8 is a broken-away side view of a section of the tubing showing the visual indictor as a series of dots;

FIG. 9 is a broken-away side view of a section of the tubing showing the visual indictor as a series of arrows;

3

FIG. 10 is a broken-away side view of a section of the tubing showing the visual indictor as a series of v-shaped tracks;

FIG. 11 is a longitudinal end view of the tubing showing the visual indictor embedded within the tubing; and FIG. 12 is a transverse cross section view showing a visual and tactile indicator embossed on the tubing.

DETAILED DESCRIPTION OF THE PREFERRED EMBODIMENTS

The method and apparatus of this invention are illustrated in FIGS. 1–12 and referenced generally therein by the numeral 10. The apparatus, method, and inventive elements or components thereof are generally referred to interchangeably in this specification as the penile prosthesis 10 for convenience.

Referring to FIGS. 1–4, representative examples of conventional penile prostheses 10 of the type known to the art with which the invention herein may be utilized are shown in basic detail. The fabrication and use of such penile prostheses 10 is described more fully in the art identified above, such as in U.S. Pat. No. 5,167,611 to Cowan, U.S. Pat. No. 5,250,020 to Bley, and U.S. Pat. No. 5,062,417 to Cowen which are incorporated herein by reference as though fully set forth.

Figure 1:
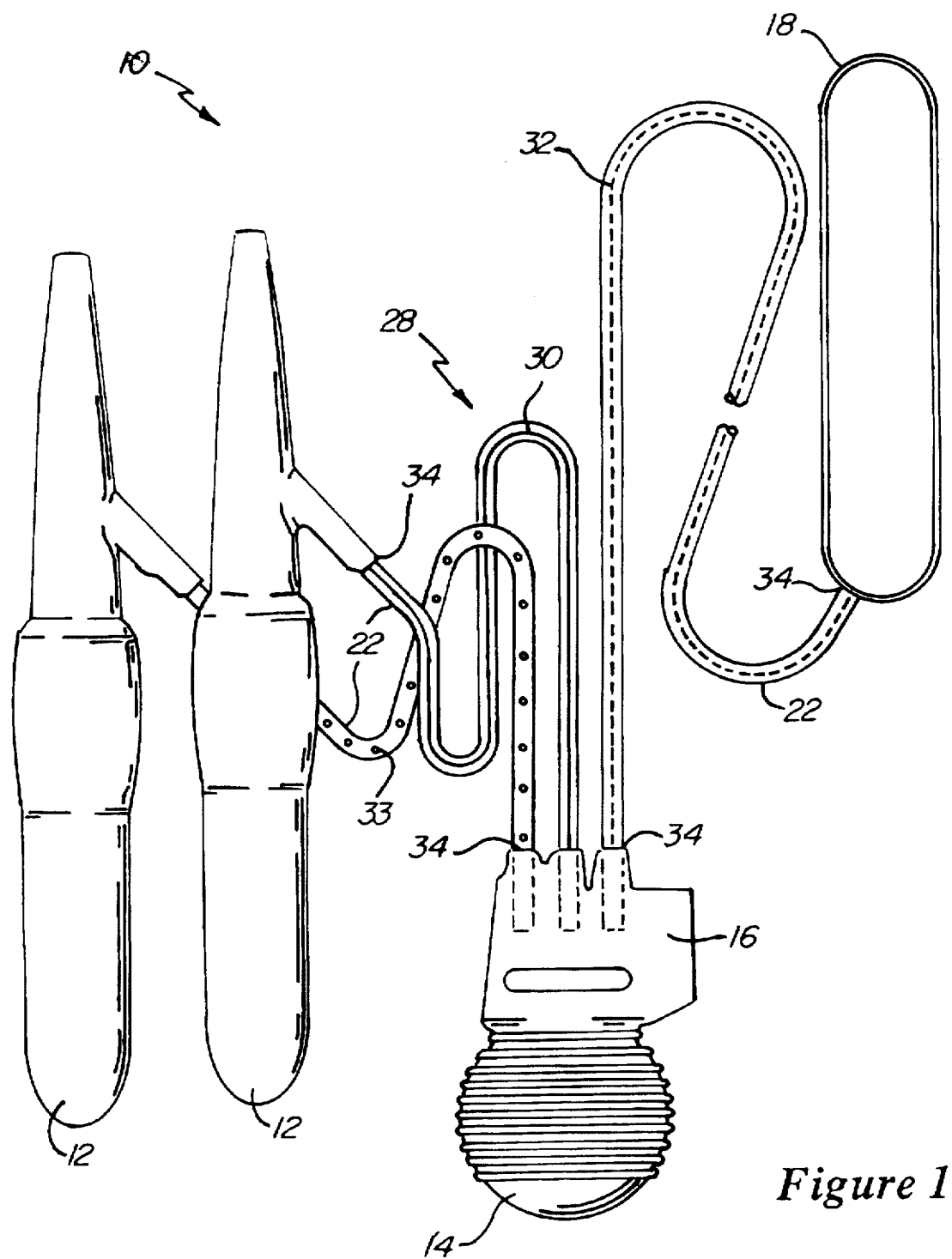
FIG. 1 is a side view of one embodiment of the penile prosthesis of this invention showing the components and tubing in a normal "untwisted" orientation without torque applied on the tubing.
Figure 2:
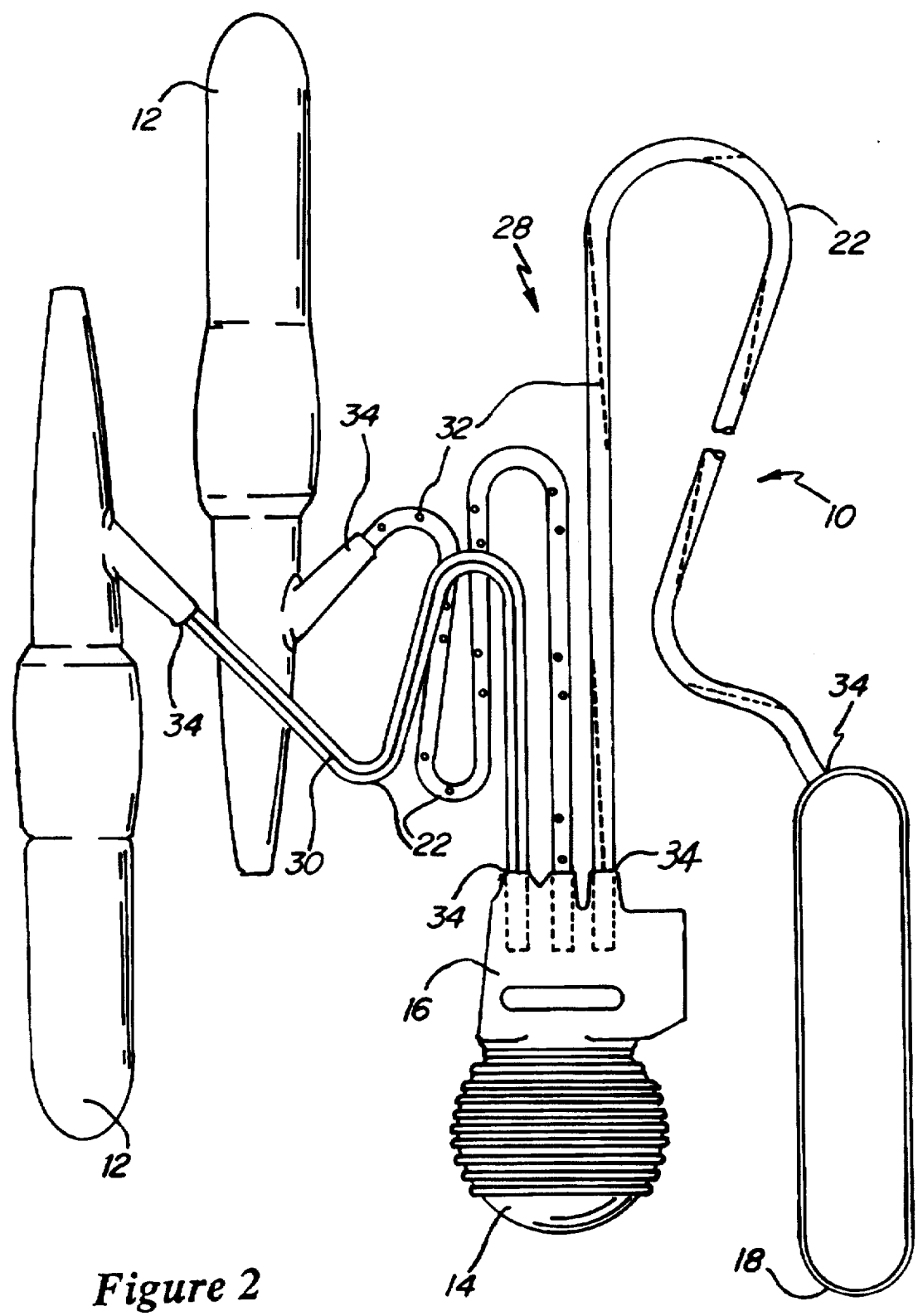
FIG. 2 is a side view of the embodiment of FIG. 1 showing the right-most cylinder and reservoir rotated and the corresponding tubing twisted.
Figure 3:
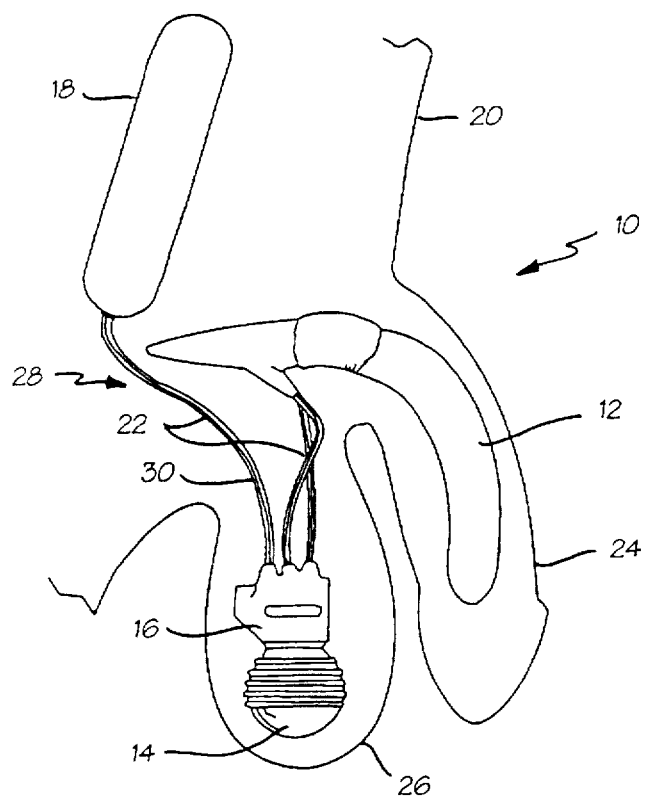
FIG. 3 is a diagrammatic view of the penile prosthesis of FIG. 1 implanted in a patient.

Referring particularly to FIGS. 1–3, one embodiment of such a penile prosthesis 10 includes a pair of inflatable chambers or cylinders 12, a pump 14 having a valve block 16, and a remote reservoir 18 containing a supply of the fluid (not shown) utilized by the patient 20 to selectively inflate the cylinders 12. The valve block 16 has a plurality of valves (not shown) associated therewith for controlling the antegrade and retrograde-flow of the fluid between the reservoir 18, pump 14, and cylinders 12. Such a design is representative of the Cowan '611 and Bley '020 patents identified above.

The fluid is conducted or transported between the reservoir 18, pump 14, and cylinders 12 via a plurality of tubing members 22. In the embodiment shown in FIGS. 1–3, two tubing members 22 are utilized to form fluid conduits between the two cylinders 12 and the valve block 16, and one tubing member 22 is utilized to form a fluid conduit between the valve block 16 and the reservoir 18. The valve block 16 and pump 14 are formed integrally, either by being fabricated unitarily or bonded or otherwise operatively connected to one another.

As shown in FIG. 3, the cylinders 12 are implanted within the corpora cavernosa of the penis 24 of the patient 20, while the pump 14 and valve block 16 are disposed within the scrotum 26, and the reservoir 18 is located remotely such as behind the pubic wall or within the stomach cavity of the patient 20.

Figure 4:
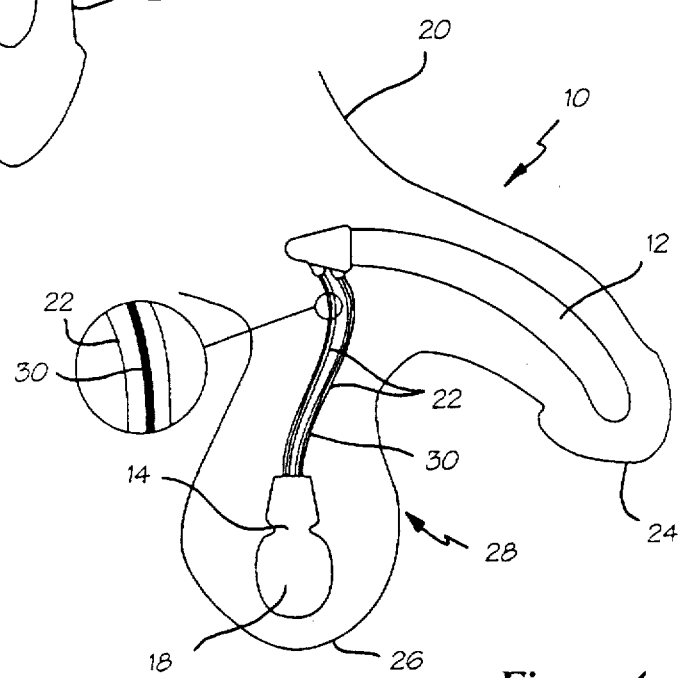
FIG. 4 is a diagrammatic view of an alternate embodiment of the penile prosthesis in which the pump and reservoir are combined into a single component.

Referring to FIG. 4, an alternate embodiment is shown in which the reservoir 18, pump 14, and valve block 16 are formed integrally, and are disposed within the scrotum 26 of the patient 20. Such a configuration is representative of the Resipump™ design produced by the assignee of the present invention or the Cowen '417 patent identified above, and may similarly be accomplished using a pressurized or displacement-style pump reservoir 18 rather than a pump 14 as previously taught in the art.

In each such embodiment, the various components 12–18 are fabricated from a medical grade material using conventional molding techniques as described and known to those skilled in the art. The tubing members 22 are similarly fabricated from a medical grade material, and may either be fabricated integrally with those components 12–18 or operatively connected in fluid communication with such components 12–18 subsequent to their molding using conventional bonding techniques and compatible adhesives. The respective dimensions, tolerances, and parameters of the components 12–18 and tubing 22 may be determined according to or dictated by the requirements of the particular application. However, it should be understood that the tubing members 22 will generally be relatively thin and flexible, and although the elastic modulus of each tubing member 22 may be sufficiently great that torsional forces or torque applied to the tubing members 22 and imparted to the corresponding components 12–18 will cause tearing or separation at the junction points 34, as well as kinking or looping of the tubing members themselves 22, the elastic modulus is sufficiently low so that the tubing members 22 when twisted do not impart sufficient torque onto the components 12–18 given the relative weights or masses of those components 12–18 (particularly when partially or wholly filled with the inflation fluid) so that a person holding a pair of the components 12–18 in their hands would necessarily notice that torque due to any physical or tactile sensation. A representative example would be a prosthesis 10 in which a 75 cubic centimeter volume reservoir 18 has a dry weight of 9 grams and a filled weight of 84 grams, the pump 14 has a dry weight of 12 grams and a filled weight of 16 grams, and the cylinder 12 has a dry weight of 10 grams and filled weight of 29 grams.

Referring again to FIGS. 1 and 2, it may be seen that the tubing members 22 are marked with an indicator 28 such as a stripe 30 or a series of linearly-aligned indicia 32 or indices. The first embodiment of the method and apparatus 10 are described herein with reference to an indicator 28 that is observed or sensed visually by the operator.

The stripe 30 or series of indicia 32 are applied to the tubing members 22 in any one of a variety of manners known to the art, such as by printing onto the exterior surface of the tubing members 22, molding a raised or detented surface integral with the tubing members 22, etching using a chemical or laser technique, or longitudinally dying a discrete cross-sectional portion of the tubing member 22 embedded with its wall during the extrusion of that tubing member 22. In instances where the stripe 30 or series of indicia 32 are applied using a physical imprint (i.e., molding or etching) rather than a printed or embedded imprint, it may be desirable to apply a visible coloring or tint to the imprint to render it easily distinguishable from the remainder of the tubing member 22.

It may also be deemed preferable in some applications to utilize different types or visually distinguishable variations in the indicator 28 on separate tubing members 22 within the same prosthesis 10, thereby more readily differentiating the tubing members 22 from one another.

Referring particularly to FIG. 1, the stripe 30 or series of indicia 32 are shown applied to the tubing members 22 of a prosthesis 10 in which the components 12–18 are in proper orientation relative to one another and the tubing members 22 are not rotated, twisted, or otherwise subject to torque. The tubing members 22 thereby do not apply torsional forces to the junction points 34 between those components 12–18 and the tubing.

In contrast, FIG. 2 shows the same prosthesis 10 in which the right-most cylinder 12 and the reservoir 18 have been rotated or twisted several times relative to the valve block 16 and pump 14, and the indicators 28 on the corresponding tubing members 22 readily display both the degree and orientation of the twisting to the physician who implants that prosthesis 10.

Referring particularly to FIGS. 3 and 4, two embodiments of the prosthesis 10 as described above are shown implanted within the patient 20, with the indicators 28 on the tubing members 22 visually displaying that the components 12–18 are in proper orientation relative to one another and the tubing members 22 are not rotated, twisted, or otherwise subject to torque forces.

Referring particularly to FIGS. 5–12, various types of indicators 28, both visual and tactile that may be utilized according to the subject invention are shown. In FIG. 5, a single continuous stripe 30 is shown applied to the exterior surface of the tubing member 22. Alternately, the continuous stripe 30 may be embedded into or embossed onto a portion of the cross-section of the tubing member 22 during or after extrusion as shown in FIGS. 11 and 12, respectively, either by dying the elastomeric material being extruded, inserting a visually or tactilely distinguishable filament prior to curing, molding the material to form a protruding portion, or coating a visually or tactilely distinct material which extends above the surface of the tubing 22.

In FIG. 6, the indicator 28 is a parallel pair of continuous stripes 30. In FIGS. 7–10, the indicator 28 is composed of a series of indicia 32 forming a generally linear aligned array, including dashes, dots, arrows, and v-shaped tracks, respectively. The series of indicia 32 should be spaced and shaped such that the degree and orientation of any rotation or twisting of the tubing members 22 would remain readily apparent to a technician inspecting or handling the prosthesis 10 subsequent to manufacturing, and to a physician or other medical personnel during the implantation procedure. While the series of indicia 32 may be a plurality of substantially uniform or identical symbols, the size, shape, or orientation of those symbols may optionally change progressively from one end of the path to the other, or the symbols may also serve a secondary function or communicate additional information. For example, the series of indicia 32 could comprise printed letters spelling a phrase or sentence such as "rotate cylinder to untwist this tube" or "rotate reservoir to untwist this tube" that could be repeated several times. Each indicator 28 and their corresponding components 12–18 could each be separately color coded to facilitate the reorientation process.

In operation, the penile prosthesis 10 is fabricated and assembled such that in completed form the components 12–18 are oriented such that no torque or torsional forces are applied to the tubing members 22, and each indictor 28 traverses a generally linear path that is continuously visible to a person from a given vantage point or perspective without that indicator 28 twisting or curving around the corresponding tubing member 22. The prosthesis 10 is inspected, packaged, and transported to a location where it will be implanted within a patient 20. The physician or other medical personnel removes the prosthesis 10 from its packaging and prepares the prosthesis for implantation, including the step of visually inspecting the tubing members 22 to verify that the indicators 28 (and therefore the tubing members 22 themselves) are in an untwisted configuration.

In the event that prior to or during the implantation procedure the physician or other medical personnel observes that the indicators 28 evidence that one or more of the tubing members 22 have become twisted or disoriented, that person will manually manipulate, rotate, or reorient one or more of the corresponding components until the corresponding indicator 28 evidences that the tubing members 22 have been untwisted and that no excessive torque or torsional forces are therefore being applied to the tubing members 22 relative to the components 12–18.

While a particular level or degree of torque that constitutes an excessive amount may not be measured or determined in each case, it is readily apparent to those of ordinary skill in the art that returning the indicator 28 to a condition in which it traverses the predetermined linear path will ensure that substantially no torque is applied to the tubing members 22, and certainly not excessive torque.

In practice, it may only be necessary for the operator to actually manipulate or move one of the components 12–18 in order to untwist the corresponding tubing member 22 or tubing members 22, while in other situations several or all of the components may need to be reoriented, rotated, or moved translationally in order to untwist the corresponding tubing members 22. In either event—whether several or only one component 12–18 is actually manipulated—it may be said that a first component 12–18 and a second component 12–18 between which the tubing member 22 is connected are manipulated relative to one another in the process of untwisting the tubing member 22 and relieving the torsional forces applied thereto.

It may also prove suitable in some applications for the tubing members 22 to be marked with a tactile indicator—in place of or in addition to the visual indicator—which may be sensed or observed by the operator through tactile contact using a finger or other suitable means.

In such a case, the indicator 28 could be fabricated as a raised or recessed portion of the outer surface of the tubing member 22 conforming to the the same location and pattern as the stripe 30 or series of linearly-aligned indicia 32 such as shown in FIGS. 1, 2, and 5–10 for exemplary pruposes. The tubing member 22 may be molded or extruded with a raised or recessed indicator 28 that is then printed or marked with the visual indicator, or the imbedded indicator such as the stripe 30 of FIG. 11 could include a partially raised surface extending radially outward relative to the outer surface of the tubing member 22 as in FIG. 12. Alternately, the indicator 28 could be fabricated using a material having a different coefficient of tactile friction compared with the tubing member 22 to provide a tactile stimulus to the user when a finger is run along the tubing member 22. This different coefficient of tactile friction could be an higher or lower differential affinity for latex compared to silicone such that a latex-gloved finger will note the tactile difference even when the tubing member 22 is wet. The indicator 28 could be imbedded in the wall of the tubing member 22, or coated or marked onto the tubing member 22 in a manner similat to application of a visual indicator. Alternately, the tactile indicator could conform to a completely different pattern than the visual indicator, such as a line of dots extending parallel to or within an area bounded by the stripe 30. In such a case, orienting the tactile indicator at an angle relative to the visual indicator would permit the user to simultaneously detect both, with the user's finger contacting the tactile indicator but not obstructing the visual indicator while the operator's finger is run along the tubing member 22 to sense or detect the orientation of the tactile indicator.

An embodiment could be constructed which would permit aural sensing of the indicator 28, such as providing a magnetic stripe 30 and a reader (not shown) that may be run along the surface of the tubing member 22, and will emit a audible pitch or tone that is generally proportional to the displacement between the reader and indicator 28, so that as the displacement between the stripe 30 and reader varies the emitted tone will also vary in a characteristic manner so that the operator may sense the variation and recognize that the tubing member 22 is twisted. The output signal from the reader could also be converted into a visible display rather than an audible output, and a record made to verify that the condition of the tubing member 22 was verified during the procedure and fell within an predetermined acceptable range.

While the preferred embodiments of the above penile prosthesis 10 having an indicator 28 thereon have been described in detail with reference to the attached drawings Figures, it is understood that various changes and adaptations may be made in the penile prosthesis 10 without departing from the spirit and scope of the appended claims.

What is claimed is:

1. A method of implanting a penile prosthesis in a patient, the penile prosthesis being implanted by an operator, the method comprising:
   (a) providing the penile prosthesis including a first component, a second component, and a conduit member fluidly connecting the first component to the second component, the conduit member having a visible indicator thereon, the visible indicator traversing a predetermined path and being visible to the operator from a given perspective, the visible indicator evidencing to the operator whether the conduit member is twisted such that torque is applied thereto;
   (b) observing the visible indicator on the conduit member to determine based upon such visual observation whether the conduit member is twisted so as to apply excessive torque thereto; and
   (c) manipulating the first component and the second component relative to one another such that the conduit member is not twisted so as to apply excessive torque thereto, and such that the visible indicator traverses a path evidencing to the operator that the conduit member is not twisted so as to apply excessive torque thereto.

2. The method of claim 1 wherein the visible indicator is a generally continuous stripe.

3. The method of claim 2 wherein both the predetermined path and the path evidencing to the operator that the conduit member is not twisted is a generally linear line.

4. The method of claim 3 wherein the conduit member has a length and the generally continuous stripe is visible to the operator along substantially all of said length of the conduit member from the given perspective.

5. The method of claim 1 wherein the visible indicator is a plurality of generally continuous stripes.

6. The method of claim 1 wherein the visible indicator is a series of indicia.

7. The method of claim 6 wherein the predetermined path is a substantially linear line and the series of indicia are generally aligned along said substantially linear line.

8. The method of claim 6 wherein the series of indicia are a plurality of dashes.

9. The method of claim 6 wherein the series of indicia are a plurality of dots.

10. The method of claim 6 wherein the series of indicia are a plurality of arrows.

11. The method of claim 6 wherein the series of indicia are a plurality of symbols substantially identical with one another.

12. The method of claim 1 wherein the first component and the second component each have a mass that is significantly greater relative to a mass of the conduit member, and the conduit member is substantially flexible, such that the torque applied to the conduit member when the conduit member is twisted is not readily ascertainable by tactile sensation when the operator holds the first component or the second component or both.

13. The method of claim 1 wherein the first component is an inflatable cylinder, and the second component is a pump.

14. The method of claim 13 wherein the pump further has a valve block, and wherein the conduit member is connected to the valve block.

15. The method of claim 1 wherein the first component is a fluid reservoir, and the second component is a pump.

16. The method of claim 1 wherein the conduit member is a flexible tubing.

17. The method of claim 16 wherein the flexible tubing is a medical grade elastomeric material.

18. A penile prosthesis for implantation within a patient, the penile prosthesis comprising:
   a first component;
   a second component; and
   a conduit member connected to and extending between the first component and said second component so as to provide fluid communication therebetween, the conduit member having a visible indicator thereon, the visible indicator traversing a predetermined path and being visible to the operator from a given perspective, the visible indicator evidencing to the operator whether the conduit member is twisted such that excessive torque is applied thereto and enabling the operator to manipulate the first component and the second component relative to one another such that the conduit member is not twisted so as to apply excessive torque thereto, and such that the visible indicator traverses a path evidencing to the operator that the conduit member is not twisted so as to apply excessive torque thereto.

19. The penile prosthesis of claim 18 wherein the first component is an inflatable cylinder, the second component is a pump, and the conduit member is a tubing member.

20. The penile prosthesis of claim 18 wherein the first component is a fluid reservoir, the second component is a pump, and the conduit member is a tubing member.

21. The penile prosthesis of claim 18 wherein the operator has a finger and the penile prosthesis further comprises:
   a tactile indicator traversing a second predetermined path and being sensed by the operator running the finger along the conduit member, the tactile indicator evidencing to the operator whether the conduit member is twisted such that torque is applied thereto.

22. A method of implanting a penile prosthesis in a patient, the prosthesis being implanted by an operator having a finger, said method comprising:
   (a) providing the penile prosthesis including a first component, a second component, and a conduit member fluidly connecting said first component to said second component, the conduit member having a tactile indicator thereon, the tactile indicator traversing a predetermined path and being sensed by the operator running the finger along the conduit member, the tactile indicator evidencing to the operator whether the conduit member is twisted such that torque is applied thereto;
   (b) sensing the tactile indicator on the conduit member by running the finger along the conduit member to determine based upon such sensed observation whether the conduit member is twisted so as to apply excessive torque thereto; and (c) manipulating the first component and the second component relative to one another such that the conduit member is not twisted so as to apply excessive torque thereto, and such that the tactile indicator traverses a path evidencing to the operator that the conduit member is not twisted so as to apply excessive torque thereto.

23. The method of claim 22 further comprising:

(a) sensing said tactile indicator on the conduit member by running the finger along the conduit member after the first component and the second component have been manipulated relative to one another to determine based upon such sensed observation that the conduit member is not twisted so as to apply excessive torque thereto.

24. A method of implanting a penile prosthesis in a patient, the penile prosthesis being implanted by an operator, the method comprising:

(a) providing the prosthesis including a first component, a second component, and a conduit member fluidly connecting the first component to the second component, the conduit member having an indicator thereon which may be sensed by the operator, the indicator traversing a predetermined path and evidencing to the operator when sensed whether the conduit member is twisted such that torque is applied thereto;

(b) sensing the indicator on the conduit member to determine based upon such sensed observation whether the conduit member is twisted so as to apply excessive torque thereto; and (c) manipulating the first component and the second component relative to one another such that the conduit member is not twisted so as to apply excessive torque thereto, and such that the indicator traverses a path evidencing to the operator when sensed that the conduit member is not twisted so as to apply excessive torque thereto.

25. The method of claim 24 wherein the indicator is a visual indicator.

26. The method of claim 24 wherein the indicator is a tactile indicator.

* * * * *

UNITED STATES PATENT AND TRADEMARK OFFICE
CERTIFICATE OF CORRECTION

PATENT NO. : 5,895,424
DATED : April 20, 1999
INVENTOR(S) : Martin T. Steele, Sr., Timothy B. Petrick and Michael J. Daugherty It is certified that error appears in the above-identified patent and that said Letters Patent is hereby corrected as shown below:

Column 9,
Line 19, after "the" but before the word prosthesis, please insert -- penile --, so that it reads as follows:

(a) providing the penile prosthesis including a . . .

Signed and Sealed this

Twenty-third Day of October, 2001

Attest:

NICHOLAS P. GODICI
Attesting Officer   Acting Director of the United States Patent and Trademark Office